United States Patent [19]

Baker et al.

[11] 4,148,927

[45] Apr. 10, 1979

[54] DIALKYL AMINO ETHYL AMIDES, THEIR SALTS AND THEIR USE AS ANTI-RIPENING AGENTS

[75] Inventors: Don R. Baker, Orinda; Daniel L. Hyzak, Saratoga, both of Calif.

[73] Assignee: Stauffer Chemical Company, Westport, Conn.

[21] Appl. No.: 839,470

[22] Filed: Oct. 4, 1977

[51] Int. Cl.$^2$ .................. A23L 3/34; C07C 103/44; C07C 103/82; C07D 307/68

[52] U.S. Cl. .................. 426/333; 260/347.3; 260/404.5 DR; 260/501.17; 260/558 R; 260/561 R; 260/561 N; 426/321

[58] Field of Search .................. 260/347.3, 404.5 PA, 260/558 R, 561 R, 561 N, 501.17; 426/321, 333

[56] References Cited

U.S. PATENT DOCUMENTS

| | | | |
|---|---|---|---|
| 1,677,544 | 7/1928 | Gams et al. | 260/558 R |
| 2,338,178 | 1/1944 | Graenacher et al. | 260/561 R X |
| 3,370,962 | 2/1968 | Farhi et al. | 426/321 X |
| 3,436,463 | 4/1969 | Mayhew et al. | 260/561 B X |
| 3,469,965 | 9/1969 | Bruce et al. | 426/321 X |
| 3,644,374 | 2/1972 | Buijle et al. | 260/558 R X |
| 3,661,868 | 5/1972 | Barron | 260/561 N X |
| 3,935,182 | 1/1976 | Jefferies et al. | 260/561 R X |
| 4,021,224 | 5/1977 | Pallos et al. | 260/561 R X |

FOREIGN PATENT DOCUMENTS

| | | | |
|---|---|---|---|
| 1359603 | 3/1964 | France | 260/558 R |
| 1364225 | 5/1964 | France | 426/321 |

OTHER PUBLICATIONS

Tchoubar, Chemical Abstracts, vol. 53 (1959) 4310c.
Tkaczynski, Chemical Abstracts, vol. 68 (1968) 104,497n.
Cassebaum et al., Chemical Abstracts, vol. 80 (1974) 82,762p.

*Primary Examiner*—Richard Raymond
*Attorney, Agent, or Firm*—Edwin H. Baker

[57] ABSTRACT

Compounds of the formula

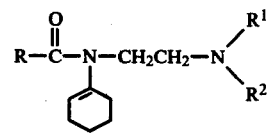

in which R is alkyl, furanyl, phenyl and isopropenyl and $R^1$ and $R^2$ are alkyl, or their amine salts and their use in retarding the ripening of picked fruits, vegetables and other merchantable materials of plant origin.

8 Claims, No Drawings

DIALKYL AMINO ETHYL AMIDES, THEIR SALTS AND THEIR USE AS ANTI-RIPENING AGENTS

BACKGROUND OF THE INVENTION

This invention relates to certain novel dialkyl amino ethyl amides, their amine salts and their use in retarding the ripening of picked fruits, vegetables and other merchantable materials of plant origin.

In the transport of freshly picked unripe fruits, vegetables and other merchandise of a plant nature from their place of origin and during the storage of such merchandise prior to its sale to the consumer, the natural ripening or maturation of the fruit, or vegetable (i.e., the further physiological activity of the tissues) must be controlled and minimized. For example, the distances and time involved in transportation of fruit produced renders it necessary to pick the fruit in unripe condition with the hope that the ripening process can be controlled until the fruit is ready for display or delivery at the consumer point of acceptance. A source of economic loss to the fruit and vegetable grower arises from the necessity of having to pick certain fruits and vegetables such as citrus fruits, bananas, peppers, and the like while they are still green. They are picked in this condition so that they may reach the consumer before over-ripening occurs. Since these fruits and vegetables must thus be harvested before the maximum weight gain occurs, there is considerable economic loss to the grower. It should also be noted that fruits and vegetables picked before they are completely ripe lose palatability.

Control of ripening is usually achieved by means of refrigeration which lowers the general level of metabolism of the plant or vegetable. In addition, it is common practice to provide adequate ventilation in the environment in which the material is stored. However, such procedures often do not delay the ripening long enough causing loss of merchantable fruit, especially when unforeseen transportation delays are encountered. An embodiment of this invention provides a process which delays the ripening of fruits and vegetables so that they may be picked and shipped at a later stage of ripening, and also to retard the sprouting of tubers while in storage.

DESCRIPTION OF THE INVENTION

The amine compounds of the present invention correspond to the structural formula:

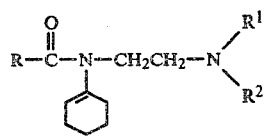

in which R is alkyl having 1 to 12 carbon atoms, preferably 4 to 10 carbon atoms, most preferably n-heptyl, n-pentyl and n-decyl, furanyl, preferably 2-furanyl, phenyl and isopropenyl, $R^1$ and $R^2$ are independently alkyl having 1 to 4 carbon atoms, preferably the same and more preferably both ethyl.

The amine compounds of this invention also can be utilized for their stated utility as the amine salts of hydrochloric acid, hydrobromic acid, sulfuric acid, phosphoric acid or acetic acid.

The amine salts of these acids are equally useful in retarding the ripening of picked fruits, vegetables and other merchantable materials of plant origin and can be represented by the following structural formula:

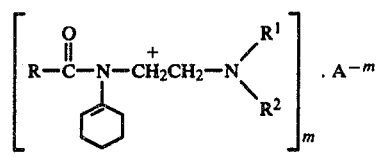

where R, $R^1$ and $R^2$ are as defined and A is the anion chloride, bromide, acetate, sulfate or phosphate; and m is 1, 2 or 3. Thus, when A is chloride, bromide or acetate, m is 1; when A is sulfate, m is 2 and when A is phosphate m is 3.

The compounds of this invention can be prepared according to the following general reaction:

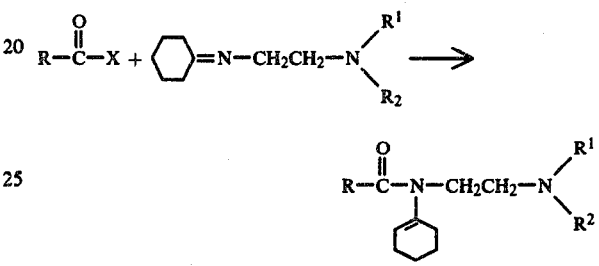

in which R, $R^1$ and $R^2$ are as defined and X is chlorine or bromine.

Generally, the reaction is carried out by slowly adding about an equimole amount of the acid chloride or bromide reactant to the amine reactant, preferably to a solution of the amine reactant, and an excess of an acid halide acceptor at a temperature between about −80° C. and about 25° C., preferably between about 0° C. to about 25° C., preferably with stirring. The temperature of the reaction mixture is then allowed to rise to a higher temperature to complete the reaction. The desired reaction product is recovered and purified by conventional techniques.

If the hydrogen chloride or hydrogen bromide salt of the compounds of this invention is desired, then no acid halide acceptor is used in the above-described reaction.

If the sulfuric acid, phosphoric acid or acetic acid salt is desired, then the amine compound is prepared as described above and is then neutralized with sulfuric, phosphoric or acetic acid, respectively.

The following example teaches the synthesis of a representative compound of this invention.

EXAMPLE I

Ethyl-N-(Diethylaminoethyl)-2-(-1-Cyclohexenyl)-Malonamate

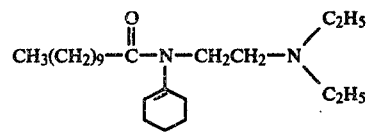

This example teaches the synthesis of a representative compound according to the general reaction scheme.

First, 4 grams (0.020 mole) diethylaminoethyl cyclohexylidene amine, 100 milliliters dry methylene chloride, and 3.13 milliliters triethylamine were combined in a flask. Next, 4.6 milliliters (0.020 mole) undecanoyl chloride was added at −0° C. with stirring. The temperature was allowed to rise to room temperature. The reaction mixture was then washed with two 200 milliliter portions of water. The organic phase was dried over MgSO$_4$. The organic solution was stripped in vacuum to yield 6.8 grams of the desired product. $n_D^{30}$ 1.4735.

The following is a table of certain selected compounds that are preparable according to the procedure described hereto. Compound numbers are assigned to each compound and are used throughout the remainder of the specification.

TABLE I

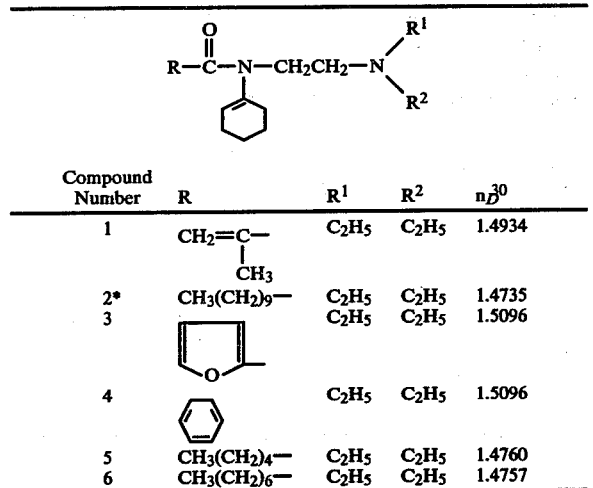

| Compound Number | R | R$^1$ | R$^2$ | $n_D^{30}$ |
|---|---|---|---|---|
| 1 | CH$_2$=C(CH$_3$)— | C$_2$H$_5$ | C$_2$H$_5$ | 1.4934 |
| 2* | CH$_3$(CH$_2$)$_9$— | C$_2$H$_5$ | C$_2$H$_5$ | 1.4735 |
| 3 | (furanyl) | C$_2$H$_5$ | C$_2$H$_5$ | 1.5096 |
| 4 | (phenyl) | C$_2$H$_5$ | C$_2$H$_5$ | 1.5096 |
| 5 | CH$_3$(CH$_2$)$_4$— | C$_2$H$_5$ | C$_2$H$_5$ | 1.4760 |
| 6 | CH$_3$(CH$_2$)$_6$— | C$_2$H$_5$ | C$_2$H$_5$ | 1.4757 |

*Prepared in Example I

Anti-Ripening Evaluation Test

The compounds of Table I were found to be useful in retarding the ripening of picked fruits, vegetables and other merchantable material of plant origin according to the following described evaluation test.

First, a candidate compound is formulated for testing by dissolving it in 10 milliliters of acetone and then diluting with 90 milliliters of water to yield stock solutions of 1000 and 5000 parts per million of the chemical. Appropriate dilutions are made from the 1000 and 5000 parts per million stock solutions to prepare lower concentrations of 10, 100 and 500 parts per million. Finally, 0.01% by weight of the wetting agent, Tween 20® (polyoxyethylene sorbitan monolaurate), is added to the treatment solution that is to be used in the test.

Bananas are used in the anti-ripening test and are obtained from Ecuador and Costa Rica and are subjected to the testing procedures approximately 10 to 14 days after harvest. They were completely green and of a uniform diameter of about one and one-half inches.

Next, the treatment solution is transferred into a plastic bag and the fruit is immersed and shaken for 30 seconds. In each test, two replicates are used per treatment and four replicates for controls. After treatment, the bananas are placed in a forced-draft hood to evaporate the treatment solution. After drying, the bananas are placed in sealable plastic bags which contain a one inch diameter hole for gaseous exchange. The bags are stored throughout the test period in a controlled environmental chamber at 16° C., 40 to 50% relative humidity, and in complete darkness for 14 days. After the selected period of time, the bananas are inspected for their degree of ripeness. The ripeness rating system that is used is based on the following scale: 1 = green, 2 = breaker, 3 = light green or yellow, 4 = table ripe, 5 = over-ripe and 6 = spoiled.

The degree of activity of certain selected compounds is indicated in Table II.

TABLE II

| Compound Number | Concentration (parts per million) | Days | Degree of Ripeness* After Treatment |
|---|---|---|---|
| Control (1 − 6) | — | 14 | 4 |
| 1 | 500 | 14 | 1 |
| 2 | 500 | 14 | 1 |
| 3 | 500 | 14 | 3 |
| 4 | 500 | 14 | 3 |
| 5 | 500 | 14 | 2 |
| 6 | 500 | 14 | 3 |

*1 = green
2 = breaker
3 = light green or yellow
4 = table ripe
5 = over-ripe
6 = spoiled As can be determined by a study of the data of Table II, the compounds of this invention cause a lesser degree of ripeness than their control.

The compounds of this invention can be used in concentrated form without adjuvants simply by spraying or dipping the fruit, vegetable or other merchantable material of plant origin. Preferably, the compounds are incorporated in formulations such as emulsions, suspensions, solutions or the like. In the most preferred practice of the invention, the compounds or their salts are utilized as aqueous solutions for treatment of the fruit, vegetable, etc. If necessary, a small amount of a non-aqueous solvent, such as acetone, can be used to add solution of the compound.

In addition, the formulation can contain materials such as waxes, oils, emulsifying agent, dispensing agents, wetting agents, coloring agents, fungicides, etc. These and other conventional additives for fruit or vegetable treating can be used according to procedures well known in the art.

The preferred quantity of the compounds of their salts that is employed to retard the ripening process of fruits, vegetables or other merchantable material of plant origin is from about 0.0001% to 5.0% by weight of fruit, vegetable or other material treated.

What is claimed is:

1. Compounds having the structural formula

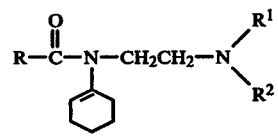

in which R is alkyl having 1 to 12 carbon atoms, furanyl, phenyl and isopropenyl, R$^1$ and R$^2$ are independently alkyl having 1 to 4 carbon atoms and their salts wherein the anion is chloride, bromide, acetate, sulfate or phosphate.

2. The compounds and their salts of claim 1 wherein R is alkyl having 4 to 10 carbon atoms, 2-furanyl, phenyl and isopropenyl, R$^1$ and R$^2$ are both ethyl.

3. The compound and its salts of claim 1 wherein R is isopropenyl, R$^1$ is ethyl and R$^2$ is ethyl.

4. The compound and its salts of claim 1 wherein R is n-decyl, R$^1$ is ethyl and R$^2$ is ethyl.

5. A method for retarding the ripening of picked fruits, vegetables and other merchantable materials of plant origin comprising contacting said fruits, vegetables and other merchantable material of plant origin with an amount effective to retard ripening of a compound having the structural formula

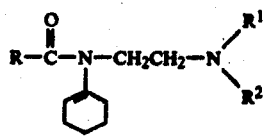

in which R is alkyl having 1 to 12 carbon atoms, furanyl, phenyl, and isopropenyl, $R^1$ and $R^2$ are independently alkyl having 1 to 4 carbon atoms and their salts wherein the anion is chloride, bromide, acetate, sulfate or phosphate.

6. A method of claim 5 wherein R is alkyl having 4 to 10 carbon atoms, 2-furanyl, phenyl and isopropenyl, $R^1$ and $R^2$ are both ethyl.

7. A method of claim 5 wherein R is isopropenyl, $R^1$ is ethyl and $R^2$ is ethyl.

8. A method of claim 5 wherein R is n-decyl, $R^1$ is ethyl and $R^2$ is ethyl.